United States Patent [19]

Oswald et al.

[11] 4,017,563
[45] Apr. 12, 1977

[54] O-ETHYL-S-N-BUTYL-O-(2- OR 3-NITROPHENYL) PHOSPHOROTHIOLATES

[75] Inventors: Alexis A. Oswald, Mountainside; Paul L. Valint, Woodbridge, both of N.J.

[73] Assignee: Ciba-Geigy AG, Basel, Switzerland

[22] Filed: Dec. 15, 1972

[21] Appl. No.: 315,389

[30] Foreign Application Priority Data

Dec. 16, 1971  Switzerland ............... 18439/71
Oct. 27, 1972  Switzerland ............... 15728/72

[52] U.S. Cl. .................. 260/954; 424/218
[51] Int. Cl.² .............................. C07F 9/18
[58] Field of Search .................... 260/954

[56] References Cited

UNITED STATES PATENTS 3,082,239   3/1963   Muhlmann et al. ........... 260/954 X
3,954,919   5/1976   Kishino et al. ................ 260/940

FOREIGN PATENTS OR APPLICATIONS 98,101   2/1964   Denmark ................. 260/954

Primary Examiner—Richard L. Raymond
Attorney, Agent, or Firm—Frederick H. Rabin; Karl F. Jorda

[57] ABSTRACT

Nitrophenylthiolphosphoric esters of the formula

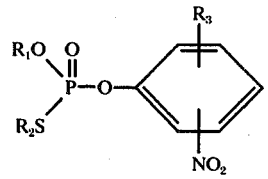

wherein
$R_1$ represents methyl or ethyl,
$R_2$ represents propyl or butyl, and
$R_3$ represents hydrogen, methyl or chlorine, processes for their manufacture and their use in pest control a novel composition of reduced mammaliam toxicity.

2 Claims, No Drawings

O-ETHYL-S-N-BUTYL-O-(2- OR 3-NITROPHENYL) PHOSPHOROTHIOLATES

The present invention relates to nitrophenylthiolphosphoric esters, processes for their manufacture and their use in pest control.

The nitrophenylthiolphosphoric esters have the formula

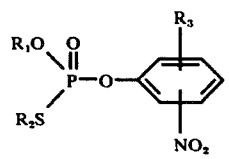

wherein $R_1$ represents methyl or ethyl, $R_2$ represents propyl or butyl prefereably n-propyl, and $R_3$ represents hydrogen, methyl or chlorine.

Therefore the formula I claims compounds, wherein $R_1$ represents methyl or ethyl, $R_2$ represents n-propyl, and $R_3$ represents hydrogen, methyl or chlorine, or wherein
  $R_1$ represents methyl or ethyl,
  $R_2$ represents n-butyl and primary i-butyl,
  $R_3$ represents hydrogen, methyl or chlorine.

This invention relates to the unusual properties of certain O,S'-dialkyl nitrophenyl thiophosphates and phenyl substituted derivatives thereof. O,O'-Dimethyl and diethyl nitrophenyl thiophosphate esters are widely known insecticides. Certain compounds of this type are extensively used for insect control, e.g. Parathion, Methyl-Parathion, Sumithion, Chlorthion, Dicapthon. Their synthesis and insecticidal action is described in the first volume of a monograph entitled "Chemie der Pflanzenschutzund Schadlingsbekampfungsmittel", edited by R. Wegler, published by Springer Verlag, New York, 1970; on pages 306 to 311. The application of such insecticides is often limited because of their high toxicity to warm-blooded animals. The search is therefore continuing to find novel thiophosphates of superior pesticidal effectiveness and at the same time reduced toxicity.

In the present invention it was found that the toxicity of such esters can be unexpectedly reduced and/or their pesticidal effectiveness maintained or suprisingly broadened by a structural isomerization involving the conversion of thiono sulfur to thiolo sulfur. For example, isomerized compositions were found to have fungicidal activity. Furthermore, it is surprisingly found that for the optimization of properties, the novel isomerized compositions should possess and O-ethyl group and an S-$C_3$ to $C_4$ alkyl group. An n-propyl or primary i-butyl group is a uniquely suitable substituent for the sulfur. These novel S-substituents were completely unsuitable in the known, O,O-dialkyl thiophosphate esters.

The structural change from the known to novel esters is exemplified by the following scheme:

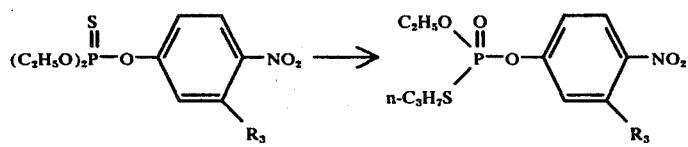

wherein $R_3$ is hydrogen, methyl or chlorine.

The novel compounds of the formula I can be manufactured by the following methods:

Phosphorylation

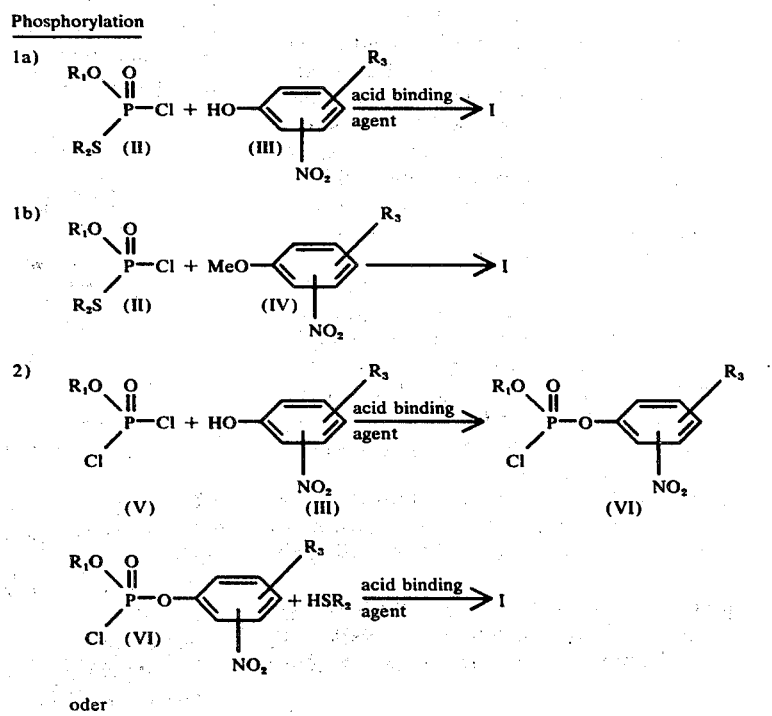

oder

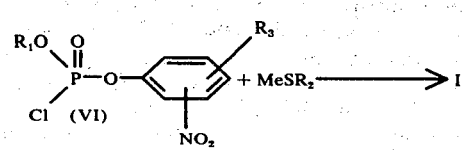

-continued

Thiophosphate Dealkylation Alkylation

3a)

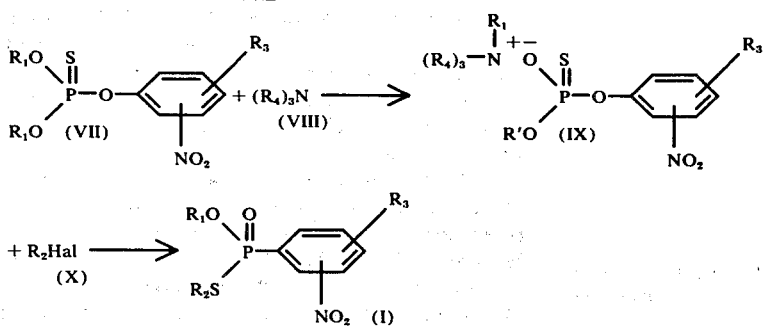

3b)

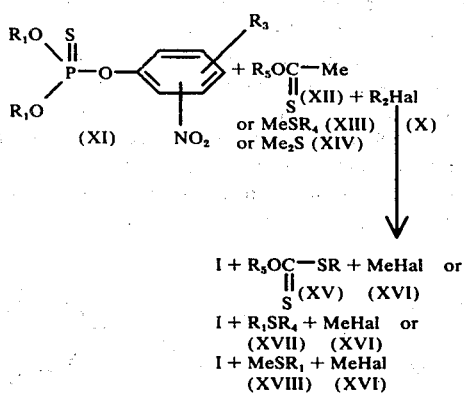

$$I + R_5OC\underset{\underset{S}{\|}}{-}SR + MeHal \text{ or}$$
$$(XV) \quad (XVI)$$
$$I + R_1SR_4 + MeHal \text{ or}$$
$$(XVII) \quad (XVI)$$
$$I + MeSR_1 + MeHal$$
$$(XVIII) \quad (XVI)$$

In the fromulae, $R_1$, $R_2$ and $R_3$ have the meanings given for the formula I, Me represents an alkali metal, in particular sodium or potassium, or the group $(R_4)_3$-$NH^+$, wherein $R_4$ represents hydrogen or alkyl, $R_5$ represents an alkyl radical and Hal represents a halogen atom, such as chlorine, bromine or iodine.

Suitable acid binding agents are: tertiary amines, e.g. trialkylamines, pyridine, pyridine bases, dialkyl anilines; inorganic bases, such as hydrides, hydroxides; carbonates and bicarbonates of alkali and alkaline earth metals. During the reactions it is sometimes necessary to use a catalyst, e.g. copper or copper chloride. Processes 1a and 1b, 2 and 3b are carried out at a reaction temperature between 0°–130° C, at normal pressure, and in solvents or diluents.

Examples of suitable solvents or diluents are: ether and ethereal compounds, such as diethyl ether, dipropyl ether, dioxan, tetrahydrofuran; amides, such as N,N-dialkylated carboxylic amides; aliphatic, aromatic, and halogenated hydrocarbons, in particular benzene, toluene, xylenes, chloroform, chlorobenzene; nitriles, such as acetonitrile; dimethyl sulphoxide; ketones, such as acetone, methyl ethyl ketone; water.

The starting materials of the formulae II to XI can be manufactured by known methods analogous to those described, for example, in J. org. Chem. 30'3217 (1965).

The compounds of the formula display a broad biocidal activity and are therefore suitable for combating various plant and animal pests and for use as plant growth regulators.

Surprisingly, however, the compounds of the formula possess in particular insecticidal and acaricidal properties which are superior to those of known analogous compounds and can be used against all development stages, e.g. eggs, larvae, pupae, nymphs and adults, of insects and representatives of the order Acarina, e.g. against insects of the families:

| | |
|---|---|
| Tettigoniida | Tenebrionidae |
| Gryllidae | Chrysomelidae |
| Gryllotalpidae | Bruchidae |
| Blattidae | Tineidae |
| Reduviidae | Noctuidae |
| Phyrrhocoridae | Lymatriidae |
| Cimicidae | Pyralidae |
| Delphacidae | Culicidae |
| Aphididae | Tipulidae |
| Diaspididae | Stomoxydae |
| Pseudococcidae | Trypetidae |
| Scarabacidae | Muscidae |
| Dermestidae | Calliphoridae and |
| Coccinellidae | Pulicidae |
| Lepidoptera | |

Beyond insects and nematodes the new compounds were found unexpectedly active against nematodes and fungi.

Acarida of the families:
Ixodidae
Argasidae
Tetranychidae and
Dermanyssidae.

The insecticidal and/or acaricidal action can be substantially broadened and adapted to suit the particular circumstances by the addition of other insecticides and/or acaricides.

Organic phosphorus compounds

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlrovinyldimethylphosphate (DICHLORVOS)
2-methoxycarbamyl-1-methylvinyldimethylphosphate (MEVINPHOS)
Dimethyl-1-methyl-2-(methylcarbamyol)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoly-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE) O,O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4,5-trichlorophenylthiophosphate (RONNEL)
O-ethyl-O,2,4,5-trichlorophenylethylthiophoasphate (TRICHLORONATE)
0,0-dimethyl-0-2,5-dichloro-4-bromophenylthiophosphate (BROMOPHOS)
O,O-dimethyl-O-(2,5-dichloro-4-iodophenyl)-thiophosphate (JODOFENPHOS)
4-tert.butyl-2-chlorophenyl-N-methyl-O-methylamidophosphate (CRUFOMATE)
O,O-dimethyl-O-(3-methyl-4-methylmercaptophenyl)-thiophosphate (FENTHION)
Isopropylamino-O-ethyl-O-(4-methylmercapto-3-methylphenyl)phosphate
O,O-diethyl-O-p-(methylsulphinyl)phenyl-thiophosphate (FENSULFOTHION)
O-p-(dimethylsulphamido)phenyl-O,O-dimthylthiophosphate (FAMPHUR) O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)-phosphate 2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxime-O,O-diethylthiophosphate (PHOXIM)
O,O-diethyl-O-(3-chloro-4-methyl-2-oxo-2-H-1-benzopyran-7-yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(dieth9xyphosphinylimino)-1,3-dithiolane
O,O-dimethyl-S-[2-methoxy-1,3,4-thiadiazol-5-(4H)-only-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)thiophosphate (DIAZINON)
O,O-diethyl-O-(2-quinoxalyl)thiophosphate
O,O-dimethyl-S-(4-oxo-1,2,3-benzotriazin-3(4H)-ylmethyl)dithiophosphate (AZINPHOSMETHYL)
O,O-diethyl-S-(4-oxo-1,2,3-benzotraizin-3-(4H)-ylmethyl)dithiophosphate (AZINPHOSETHYL)
S-[(4,6-diamino-s-traizin-2-yl)methyl]-O,O-dimethyl-dithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2-(O,O-dimethyl-phosphoryl-thiomethyl)-5-methoxy-pyrone-4-3,4-dichlorobenzyl-triphenylphosphonium-chloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-dethyl-O-[2-dimethylamino-4-methylpyrimidyl(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)

O,O-dimethyl-O-(2-chloro-4-nitrophenyl)thiophosphate (DICAPTHON)
O,O-dimethyl-O-p-cyanophenyl thiophosphate (CYANOX)
O-ethyl-O-P-Cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
dimethyl-p-(methylthio)phenylphosphate
O,O-dimethyl-O-p-sulphamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,o-diethyl-S-(carbofluorethoxy-phenylmethyl)dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin -2-sulphide
O,O-diethyl-O-(5-phenyl-3-isooxazolyl)thiophosphate
2-(diethoxyphosphinylimino)-4-methyl-1,3-dithiolane
tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
diethyl-S-2-(ethylsulphinyl)ethyl dithiophosphate (OXIDISULFOTON)
bis-O,O-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
O,O-dimethyl-O-(2,2-dichloro-1-methoxy-vinyl)phosphate
bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
diisopropylaminofluorophosphate (MIPAFOX)
O,O-dimethyl-S-(morpholinylcarbamoylmethyl)dithiophosphate (MORPHOTHION)
bismethylamidio-phenylphosphate
O,O-dimethyl-S-(benzenesulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
O-phenyl-O-p-nitrophenyl-methanethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethyl-phenyl)-thiophosphate
4,4'-bis-(O,O-dimethylthiophosphoryloxy)-diphenyl disulphide
O,O-di-(β-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene(1,5)
O-methyl-O-(2-i-propoxycarbonyl-1-methylvinyl)-ethylamidothiophosphate.

Nitrophenols and derivatives 4,6-dinitro-6-methylphenol, sodium salt [Dinitrocresol]
dinitrobutylphenol-(2,2',2")-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)

(I)-3-(2-furfuryl)-2-methyl-4-oxocyclopent-2-enyl(I)-(cis+trans)chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbamyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate 2-(1,3-dioxolan-2-yl)phenyl-N,N-dimethylcarbamate
2-(1,3dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)-phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimthylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithiolane-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethyl-carbamate
O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-acetal-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate 3-methoxymethoxy-phenyl-N-methylcarbamate
3-allyloxyhenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γHCH]
1,2,4,5,6,7,8,8-octachloro-3α,4,7,7α'tetrahydro-4,7-methylene indane [CHLORDAN]
1,4,5,6,7,8,8-heptachloro,3α,4,7,7α-tetrahydro-4,7-methylene indane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-octa-hydro-exo-1,4,endo-5,8-dimethanonaphthalene [DIFLORIN]
1,2,3,4,10,10-hexachloro-5,7-epoxy-1,4,4α,5,6,7,8,8α-octyhydro-endo-endo-5,8-dimethanonaphthalene [ENDRIN]

The active substances of the formula I are also suitable for combating representatives of the division Thallophyta, e.g. viruses, bacteria and fungi. They thus possess fungicidal properties against phytopathogenic fungi on various cultivated plants, such as cereals, maize, rice, vegetables, ornamental plants, fruit trees, vines, farm products, etc.

With the new active substances it is possible to control or destroy fungi occurring on fruit, blossom, leaves, stems, tubers and roots, and from which parts of plants which grow later then also remain free. The active substances of the formula I are active in particular against phytopathogenic fungi belonging to the following classes: oomycetes, Zygomycetes, Ascomycetes, Basidiomycetes, Denteromycetes.

In addition, the new active substances can also be used for treating seeds, fruit, tubers etc., and protecting them from fungus infections, for example from smut fungi of all kinds, such as Ustilaginales, e.g. Ustilago, Tilletia, Urocystis, Turbicinia and Phoma types.

In addition to the above cited acaricides and insecticides, it is also possible to admix the active substances of the formula I with, for example, bactericides, fungistatic agents, bacteriostatic agents, nematocides and/or e.g. the following fungicides, in order to broaden the activity spectrum:
dodecylguanidine acetate (DODINE)
pentachloronitrobenzene (QUINTOZENE)
pentachlorophenol (PCP)
2-(1-methyl-n-propyl)-4,6-dinitrophenyl-2-methyl-crotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FLOPAT)
N-(trichloromethylthio) cyclohex-4-ene-1,2-dicarboximide (CAPTAN)
N-(1,1,2,2-tetrachloroethylthio)cyclohex-4-ene-1,2-dicarboximide (CAPTAFOL)
N-methansulfonal-N-trichloromethylthio-chloroaniline
N'-dichlorofluoromethylthio-N,N-dimethyl-N'-phenyl-sulphamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramidsulphide (THIRAM)
1-oxy-3-acetyl-6-methyl-cyclohexene-(5)dione-(2,4) (DEHYDRO-ACETIC ACID)
8-hydroxyquinoline (8-QUINOLINOL)
2-dimethylalimo-6-methyl-5-n-butyl-4-hydroxy-pyrimidine
methyl-N-benzimidazole-2-yl-N-(butylcarbamoyl)carbamate (BENOMYL)
2-ethylamino-6-methyl-5N-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine
pentachlorobenzyl alcohol.

Furthermore, the compounds of the formula I are suitable for combating plant pathogenic nematodes.

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms.

Solid forms

Dusts, tracking agents, granules, coated granules, impregnated granules and homogeneous granules.

Liquid forms a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, SiO$_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, ligrain sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/ propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanolo, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, the size of the solid particles does not exceed 0.02 to 0.04 $\mu$ in wettable powders, and 0.03 $\mu$ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350° C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic and aromatic hydrocarbons, chlorinated derivatives thereof, alkyl naphthalenes, and mineral oils, singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for examle, be formulated as follows:

Dusts

The following substances are used to manufacture (a) a 5% and (b) a 2% dust:

a.

5 parts of active substance
95 parts of talcum b.

2 parts of active substance
1 part of highly disperse silicic acid
97 parts of talcum.

The active substances are mixed with the carriers and ground.

Granules

The following substances are used to produce 5% granules:

parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder

The following constituents are used for the preparation of (a) also a 40%, (b) and (c) a 25%, and (d) a 10% wettable powder:

a.

40 parts of active substance,
5 parts of sodium lignin sulphonate,
1 part of sodium dibutyl-naphthalene sulphonate,
54 parts of silicic acid.

b.

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

c.

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin.

d.

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a.

10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

b.

25 parts of active substance,
2.5 parts of epoxidised vegetable oil,
10 parts of an alkylarlysulphonate/fatty alcohol-polyglycol ether mixture
5 parts of dimethylformamide,
57.5 parts of xylene.

From these concentrates it is possible to produce, by dilution with water, emulsions of any desired concentration.

Spray

The following constituents are used to prepare a 5% spray:

5 parts of active substance,
1 part of epichlorohydrin,
94 parts of benzine (boiling limits 160° – 190° C).

EXAMPLE 1

O-ethyl-S-n-propyl-O-(3-nitrophenyl)-thiophosphoric ester

To a solution of 18.1 g of m-nitrophenol in 150 ml of benzene are added 13.3 g of triethylamine. While stirring constantly, 26.4 g of O-ethyl-S-n-propylchlorothiolphosphoric ester are added dropwise at 10°–15° C. The reaction mixture is stirred for 12 hours, then washed with water, 3% Na$_2$CO$_3$ solution and again with water, and dried over sodium sulphate. The benzene is distilled off. Molecular distillation of the residue at 135° C/0.001 Torr yields the compound of the formula

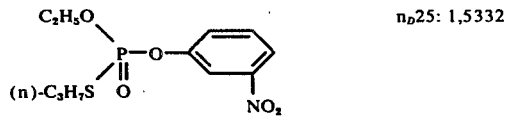

The following compounds are also manufactured in analogous manner:

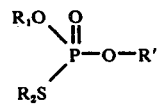

| $R_1$ | $R_2$ | R' | Physical Data |
|---|---|---|---|
| $-C_2H_5$ | $-C_3H_{7(n)}$ | 4-$NO_2$-3-$CH_3$-phenyl | $n_D25: 1.5374$ |
| $-C_2H_5$ | $-C_4H_{9(n)}$ | 3-$NO_2$-phenyl | $n_D25: 1.5272$ |
| $-C_2H_5$ | $-C_4H_{9(n)}$ | 2-$NO_2$-phenyl | $n_D25: 1.5263$ |
| $-C_2H_5$ | $-C_3H_{7(n)}$ | 2-$NO_2$-phenyl | |
| $-C_2H_5$ | $-C_3H_{7(n)}$ | 3-$CH_3$-4-$NO_2$-phenyl | $n_D25: 1.5233$ |
| $-C_2H_5$ | $-C_3H_{7(n)}$ | 2-$CH_3$-4-$NO_2$-phenyl | |
| $-C_2H_5$ | $-C_3H_{7(n)}$ | 4-$NO_2$-phenyl | $n_D25: 1.5366$ |
| $-C_2H_5$ | $-C_3H_{7(n)}$ | 3-Cl-4-$NO_2$-phenyl | $n_D25: 1.5442$ |
| $-C_2H_5$ | $-C_2H_{7(n)}$ | 4-Cl-3-$NO_2$-phenyl | $n_D23: 1.5409$ |
| $-C_2H_5$ | $-C_3H_{7(n)}$ | 2-Cl-4-$NO_2$-phenyl | |
| $-C_2H_5$ | $-CH_2CH(CH_3)_2$ | 4-$NO_2$-phenyl | |
| $-C_2H_5$ | $-CH_2CH(CH_3)_2$ | 3-$CH_3$-4-$NO_2$-phenyl | |
| $-C_2H_5$ | $-CH_2CH(CH_3)_2$ | 2-Cl-4-$NO_2$-phenyl | |

EXAMPLE 2

O-Ethyl S-1O'-4-Nitrophenyl Thiophosphate

O,O-Diethyl-O-4-nitrophenyl thiophosphate (58.2 g., 0.2 mole) and 22.4 g. (0.2 mole) of triethylenediamine were left to stir at ambient temperature for 24 hours. The resulting, viscous liquid was dissolved in 500 me. of acetonitrile and 49.2 g. (0.4 mole) of 1-bromo propane were added. The reaction mixture was heated to 70° C for 2 hours and worked up to give 25.2 g. of 82% pure product which was found surprisingly effective against fungi, specifically against bean rust.

Anal. Calcd. for $C_{11}H_{16}O_5PS$: C, 43.41; H, 5.25; P, 10.16; Found: C, 43.03; H, 5.38; P, 10.01.

EXAMPLE 3

A. Insecticidal ingest poison action

Tobacco and potato plants were sprayed with a 0.05% aqueous emulsion (obtained from a 10% emulsifiable concentrate).

After the coating had dried, the tobacco plants were populated with Egyptian cotton leaf worms (Spodoptera littoralis) and the potato plants with Colorado potato beetle larvae (Leptinotarsa decemlineata). The test was carried out at 24° C and 60% relative humidity. In the above test the compounds according to Example 1 displayed ingest poison action against Spodoptera littoralis and Leptinotarsa decemlineata.

B. Systemic insecticidal action

To determine the systemic action, rooted bean plants (Vicia fabae) were put into a 0.01% aqueous active substance solution (obtained from a 10% emulsifiable concentrate). After 24 hours, aphids (Aphis fabae) were placed on the parts of the plant above the soil. The aphids were protected from contact and gas action by means of a special device. The test was carried out at 24° C and 70% relative humidity. In the above tests the compounds according to Example I displayed insecticidal ingest posion action and systemic insecticidal action.

EXAMPLE 4

Action against Chilo suppressalis

Six rice plants at a time of the variety Caloro were transplanted into plastic pots (diameter at the top= 17 cm) and reared to a height of about 60 cm. Infestation with Chilo suppressalis larvae ($L_1$:3-4 mm long) took place 2 days after the active substance had been applied in granule form to the paddy water (rate of application: 8 kg of active substance per hectare). Evaluation of the insecticidal action ensued 10 days after application of the granules.

The compounds according to Example I were active in the above test against Chilo suppressalis.

EXAMPLE 5

Action against soil insects

Sterilised compost earth was homogeneously mixed with a wettable powder containing 25% of active substance so as to produce a rate of application of 8 kg of active substance per hectare.

Young zuccetti plants (*Cucumis pepo*)were put into plastic pots with the treated soil (3 plants per pot; diameter of pot = 7 cm). Each pot was infected immediately afterwards with 5 Aulacophora femoralis and Pachmoda or Chortophila larvae. The control was carried out 4, 8, 16 and 32 days after the larvae had been put into the soil.

At 80–100% kill after the first control, a fresh infestation with 5 larvae per pot was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I displayed action against *Aulacophora fermoralis*, Pachmoda and Chortophila larvae.

EXAMPLE 6

Action against ticks

A. *Rhicephalus bursa*

Five adult ticks or 50 tick larvae were counted into a test tube and immersed for 1 to 2 minutes in 2 ml of an aqueous emulsion from an emulsion series each containing 100, 10, 1 and 0.1 ppm of test substance. The tube was the sealed with a standardised cotton wool plug and stood on its head so as to enable the cotton wool to absorb the active substance emulsion.

In the case of the adults evaluation took place after 2 weeks, and in that of the larvae after 2 days. Each test was repeated twice.

B. *Boophilus microplus* (larvae)

Tests were carried out with 20 sensitive and 20 OPresistent larvae with a dilution series analogous to that used in test A. (The resistence refers to the tolerability of Diazinon).

In these tests the compounds according to Example 1 acted against adults and larvae of *Rhipicephalus bursa* and sensitive and OP-resistent larvae of *Boophilus microplus*.

EXAMPLE 7

Acaracidal action

*Phaseolus vulgaris* (dwarf beans) were overlaid with a piece of leaf from a mass culture of Tetranychus urticae 12 hours before the test for the acaricidal action. The mobile stages which had spread over the plants were sprayed with the emulsified test preparations from a chromatography atomiser so that the spray broth did not run off. The number of living and dead larvae, adults and eggs were evaluated after 2 to 7 days under a steroscopic microscope and the result was expressed in percentages. During the "interim", the treated plants were kept in greenhouse compartments at 25° C.

The compounds according to Example I acted in the above test against eggs, larvae and adults of Tetranychus urticae.

EXAMPLE 8

Action against soil nematodes

To test the action against soil nematodes, the active substances were applied to, and intimately mixed with soil infected with root gall nematodes (*Meloidgyne arenaria*) in the specifically indicated concentrations. Immediately afterwards, tomato cuttings were planted in the thus prepared soil in a series of tests and after a waiting time of 8 days tomato seeds were sown in another test series.

In order to assess the nematocidal action, the galls present on the roots were counted 28 days after planting and sowing respectively. The compounds according to Example I to 4 displayed good action in this test against *Meloidgyne arenaria*.

We claim:

1. The compound of the formula

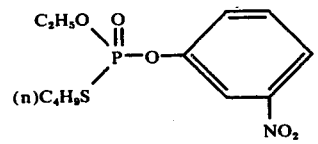

2. The compound of the formula

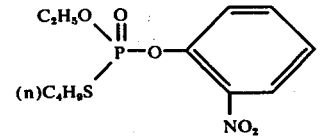

* * * * *